(12) United States Patent
Faries, Jr. et al.

(10) Patent No.: US 8,487,738 B2
(45) Date of Patent: Jul. 16, 2013

(54) METHOD AND APPARATUS FOR SECURELY STORING MEDICAL ITEMS WITHIN A THERMAL TREATMENT SYSTEM

(75) Inventors: Durward I. Faries, Jr., Las Vegas, NV (US); Bruce R. Heymann, Vienna, VA (US); David Hendrix, Ashburn, VA (US)

(73) Assignee: Medical Solutions, Inc., Chantilly, VA (US)

(*) Notice: Subject to any disclaimer, the term of this patent is extended or adjusted under 35 U.S.C. 154(b) by 1068 days.

(21) Appl. No.: 11/688,346

(22) Filed: Mar. 20, 2007

(65) Prior Publication Data

US 2007/0215018 A1    Sep. 20, 2007

Related U.S. Application Data

(60) Provisional application No. 60/783,389, filed on Mar. 20, 2006.

(51) Int. Cl.
*E05G 1/00* (2006.01)

(52) U.S. Cl.
USPC .......... 340/5.2; 340/5.73; 340/5.24; 219/494; 219/495; 219/385; 219/497

(58) Field of Classification Search
USPC ............... 340/5.2, 5.52, 52.54, 5.6, 545.6, 340/539.12; 109/38, 23; 700/236, 242, 244; 219/494, 385, 394, 395, 497, 508
See application file for complete search history.

(56) References Cited

U.S. PATENT DOCUMENTS

| | | |
|---|---|---|
| 1,479,451 A | 1/1924 | Buckstein |
| 1,659,719 A | 2/1928 | Blake |
| 1,847,573 A | 3/1932 | Rupp |
| 2,175,099 A | 10/1939 | Abbott |
| 2,214,215 A | 9/1940 | Watermann et al. |
| 2,576,874 A | 11/1951 | Acton |
| 2,701,789 A | 2/1955 | White |
| 2,713,112 A | 7/1955 | Mills et al. |
| 2,741,099 A | 4/1956 | Beane |
| 2,841,132 A | 7/1958 | Philipp |

(Continued)

FOREIGN PATENT DOCUMENTS

| | | |
|---|---|---|
| CA | 2103791 | 10/1993 |
| DE | 37 42 927 A1 | 7/1989 |

(Continued)

OTHER PUBLICATIONS

Cahill, *New Name, New Helmsman*, JEMS, Aug. 1996.

(Continued)

*Primary Examiner* — Nabil Syed
(74) *Attorney, Agent, or Firm* — Edell, Shapiro & Finnan, LLC (57) ABSTRACT

A locking mechanism for thermal treatment systems (e.g., systems heating and/or cooling solutions prior to the solutions being administered to the patient) or other medical equipment according to the present invention embodiments secures medications being stored and/or thermally treated therein. The locking mechanism includes an integrated monitoring and display system to determine and indicate the status of the thermal treatment system. The monitoring and display system includes indicator lights that allow for a visual representation indicating the locked or open states of system access doors and/or an audio system or alarm for alerting medial or other personnel to the status of the locking mechanism.

34 Claims, 4 Drawing Sheets

U.S. PATENT DOCUMENTS

| | | |
|---|---|---|
| 2,880,764 A | 4/1959 | Pelavin |
| 2,885,526 A | 5/1959 | Paulding |
| 2,910,981 A | 11/1959 | Wilson et al. |
| 2,990,875 A | 7/1961 | Samuels et al. |
| 2,994,760 A | 8/1961 | Pecoraro et al. |
| 3,051,582 A | 8/1962 | Muckler et al. |
| 3,157,727 A | 11/1964 | Hardy et al. |
| 3,193,339 A | 7/1965 | Cooper |
| 3,241,603 A | 3/1966 | Nagata |
| 3,255,812 A | 6/1966 | Bayane et al. |
| 3,293,868 A | 12/1966 | Gonzalez |
| 3,329,202 A | 7/1967 | Birman |
| 3,353,589 A | 11/1967 | Tope et al. |
| 3,386,498 A | 6/1968 | Funfstuck |
| 3,485,245 A | 12/1969 | Lahr et al. |
| 3,500,366 A | 3/1970 | Chesney et al. |
| 3,536,132 A | 10/1970 | Pecoraro et al. |
| 3,563,090 A | 2/1971 | Deltour |
| 3,590,215 A | 6/1971 | Anderson et al. |
| 3,591,290 A | 7/1971 | Zinner et al. |
| 3,596,515 A | 8/1971 | Cramer |
| 3,612,165 A | 10/1971 | Haynes |
| 3,713,302 A | 1/1973 | Reviel |
| 3,777,187 A | 12/1973 | Kohn |
| 3,826,305 A | 7/1974 | Fishman |
| 3,858,106 A | 12/1974 | Launius |
| 3,879,171 A | 4/1975 | Tulis |
| 3,940,742 A | 2/1976 | Hudspeth et al. |
| 4,024,377 A | 5/1977 | Henke |
| 4,063,551 A | 12/1977 | Sweeney |
| 4,084,080 A | 4/1978 | McMahan |
| 4,090,514 A | 5/1978 | Hinck et al. |
| 4,098,123 A | 7/1978 | Granzow, Jr. |
| 4,189,995 A | 2/1980 | Löhr et al. |
| 4,233,495 A | 11/1980 | Scoville et al. |
| 4,309,592 A | 1/1982 | Le Boeuf |
| 4,314,484 A | 2/1982 | Bowman |
| 4,318,276 A | 3/1982 | Sato et al. |
| 4,328,676 A | 5/1982 | Reed |
| 4,331,859 A | 5/1982 | Thomas et al. |
| 4,336,435 A | 6/1982 | Kashyap et al. |
| 4,364,234 A | 12/1982 | Reed |
| 4,397,648 A | 8/1983 | Knute |
| 4,407,133 A | 10/1983 | Edmonson |
| 4,419,568 A | 12/1983 | VanOverloop |
| 4,430,077 A | 2/1984 | Mittleman et al. |
| 4,432,761 A | 2/1984 | Dawe |
| 4,455,478 A | 6/1984 | Guibert |
| 4,464,563 A | 8/1984 | Jewett |
| 4,476,877 A | 10/1984 | Barker |
| 4,481,410 A | 11/1984 | Bortnick |
| 4,495,402 A | 1/1985 | Burdick et al. |
| 4,498,901 A | 2/1985 | Finch |
| 4,509,943 A | 4/1985 | Hanzawa |
| 4,522,308 A | 6/1985 | Sullivan |
| 4,523,078 A | 6/1985 | Lehmann |
| 4,529,309 A | 7/1985 | Pettersson et al. |
| 4,532,414 A | 7/1985 | Shah et al. |
| 4,533,350 A | 8/1985 | Danby et al. |
| 4,552,277 A | 11/1985 | Richardson et al. |
| 4,572,536 A | 2/1986 | Doughty |
| 4,585,441 A | 4/1986 | Archibald |
| 4,586,691 A | 5/1986 | Kozlow |
| 4,605,840 A | 8/1986 | Koopman |
| 4,625,086 A | 11/1986 | Karino |
| 4,628,186 A | 12/1986 | Bergemann et al. |
| 4,634,432 A | 1/1987 | Kocak |
| 4,647,756 A | 3/1987 | Willis |
| 4,657,004 A | 4/1987 | Coffey |
| 4,673,820 A | 6/1987 | Kamen |
| 4,674,977 A | 6/1987 | Hoselton |
| 4,678,460 A | 7/1987 | Rosner |
| 4,680,445 A | 7/1987 | Ogawa |
| 4,680,977 A | 7/1987 | Conero et al. |
| 4,705,505 A | 11/1987 | Fried |
| 4,707,587 A | 11/1987 | Greenblatt |
| 4,718,896 A | 1/1988 | Arndt et al. |
| 4,726,193 A | 2/1988 | Burke et al. |
| 4,745,248 A | 5/1988 | Hayes |
| 4,747,450 A | 5/1988 | Ikegame et al. |
| 4,801,777 A | 1/1989 | Auerbach |
| 4,808,159 A | 2/1989 | Wilson |
| 4,814,570 A | 3/1989 | Takizaki |
| 4,823,554 A | 4/1989 | Trachtenberg et al. |
| 4,823,833 A | 4/1989 | Hogan et al. |
| 4,844,397 A | 7/1989 | Skakoon et al. |
| 4,874,033 A | 10/1989 | Chatelain et al. |
| 4,883,117 A | 11/1989 | Dobbs et al. |
| 4,894,207 A | 1/1990 | Archer et al. |
| 4,904,848 A | 2/1990 | Colevas |
| 4,906,816 A | 3/1990 | Van Leerdam |
| 4,910,386 A | 3/1990 | Johnson |
| 4,923,681 A | 5/1990 | Cox et al. |
| 4,934,152 A | 6/1990 | Templeton |
| 4,934,336 A | 6/1990 | White |
| 4,935,604 A | 6/1990 | Allen et al. |
| 4,936,828 A | 6/1990 | Chiang |
| 4,961,320 A | 10/1990 | Gutmann |
| 4,991,976 A | 2/1991 | Byles |
| 4,994,021 A | 2/1991 | Smith et al. |
| 5,040,380 A | 8/1991 | Gregory |
| 5,061,241 A | 10/1991 | Stephens, Jr. et al. |
| 5,061,630 A | 10/1991 | Knopf et al. |
| 5,074,658 A | 12/1991 | Talvarides et al. |
| 5,081,697 A | 1/1992 | Manella |
| 5,096,078 A | 3/1992 | McQueeny |
| 5,103,817 A | 4/1992 | Reisdorf et al. |
| 5,106,373 A | 4/1992 | Augustine et al. |
| 5,108,372 A | 4/1992 | Swenson |
| 5,125,900 A | 6/1992 | Teves |
| 5,129,033 A | 7/1992 | Ferrara et al. |
| 5,152,755 A | 10/1992 | Yoshinori |
| 5,153,827 A | 10/1992 | Coutre et al. |
| 5,172,347 A | 12/1992 | Masuda |
| 5,183,994 A | 2/1993 | Bowles, Sr. et al. |
| 5,186,057 A | 2/1993 | Everhart |
| 5,195,976 A | 3/1993 | Swenson |
| 5,217,064 A | 6/1993 | Kellow et al. |
| 5,243,172 A | 9/1993 | Hazan et al. |
| 5,243,833 A | 9/1993 | Coelho et al. |
| 5,263,929 A | 11/1993 | Falcone et al. |
| 5,269,749 A | 12/1993 | Koturov |
| 5,276,310 A | 1/1994 | Schmidt et al. |
| 5,282,264 A | 1/1994 | Reeves et al. |
| 5,290,222 A | 3/1994 | Feng et al. |
| 5,296,684 A | 3/1994 | Essig et al. |
| 5,297,234 A | 3/1994 | Harms et al. |
| 5,315,830 A | 5/1994 | Doke et al. |
| 5,333,326 A | 8/1994 | Faries, Jr. et al. |
| 5,345,923 A | 9/1994 | Luebke et al. |
| 5,364,371 A | 11/1994 | Kamen |
| 5,364,385 A | 11/1994 | Harms et al. |
| 5,381,510 A | 1/1995 | Ford et al. |
| 5,392,025 A * | 2/1995 | Figh et al. .................. 340/547 |
| 5,397,875 A | 3/1995 | Bechtold, Jr. |
| 5,399,007 A | 3/1995 | Marconet |
| 5,408,576 A | 4/1995 | Bishop |
| 5,424,512 A | 6/1995 | Turetta et al. |
| 5,483,799 A | 1/1996 | Dalto |
| 5,494,196 A | 2/1996 | Tyner |
| 5,524,643 A | 6/1996 | Faries, Jr. et al. |
| 5,540,901 A | 7/1996 | Riley |
| 5,572,873 A | 11/1996 | Lavigne et al. |
| 5,590,648 A | 1/1997 | Mitchell et al. |
| 5,609,784 A | 3/1997 | Davenport |
| 5,653,905 A | 8/1997 | McKinney |
| 5,658,478 A | 8/1997 | Roeschel et al. |
| 5,661,978 A | 9/1997 | Holmes et al. |
| 5,707,151 A | 1/1998 | Parker et al. |
| 5,720,728 A | 2/1998 | Ford |
| 5,729,653 A | 3/1998 | Magliochetti et al. |
| 5,733,263 A | 3/1998 | Wheatman |
| 5,744,806 A | 4/1998 | Frojd |
| 5,786,568 A | 7/1998 | McKinney |
| 5,805,455 A | 9/1998 | Lipps |
| 5,816,797 A | 10/1998 | Shoenfeld |
| 5,858,303 A | 1/1999 | Schiffmann et al. |

| | | |
|---|---|---|
| 5,862,672 A | 1/1999 | Faries, Jr. et al. |
| 5,868,195 A | 2/1999 | Westbrooks, Jr. |
| 5,868,250 A | 2/1999 | Brackett |
| 5,875,282 A | 2/1999 | Jordan |
| 5,879,329 A | 3/1999 | Ginsburg |
| 5,897,207 A | 4/1999 | Hartmann |
| 5,910,210 A | 6/1999 | Violi et al. |
| 5,924,289 A | 7/1999 | Bishop, II |
| 5,954,700 A | 9/1999 | Kovelman |
| 5,961,492 A | 10/1999 | Kriesel et al. |
| 5,961,866 A | 10/1999 | Hansen |
| 5,977,520 A | 11/1999 | Madson, Jr. et al. |
| 5,986,239 A | 11/1999 | Corrigan, III et al. |
| 5,989,238 A | 11/1999 | Ginsburg |
| 6,039,926 A | 3/2000 | Goldman |
| 6,045,648 A | 4/2000 | Palmgren et al. |
| 6,102,044 A | 8/2000 | Naidyhorski |
| 6,117,122 A | 9/2000 | Din et al. |
| 6,124,572 A | 9/2000 | Spilger et al. |
| 6,158,458 A | 12/2000 | Ryan |
| 6,174,300 B1 | 1/2001 | Kriesel et al. |
| 6,175,099 B1 | 1/2001 | Shei et al. |
| 6,221,045 B1 | 4/2001 | Duchon et al. |
| 6,221,051 B1 | 4/2001 | Hjertman et al. |
| 6,248,077 B1 | 6/2001 | Elson et al. |
| 6,254,572 B1 | 7/2001 | Knipfer et al. |
| 6,259,067 B1 | 7/2001 | Faries, Jr. et al. |
| 6,315,767 B1 | 11/2001 | Dumont et al. |
| 6,316,750 B1 | 11/2001 | Levin |
| 6,334,707 B1 | 1/2002 | Ku |
| 6,371,121 B1 | 4/2002 | Faries, Jr. et al. |
| 6,384,380 B1 | 5/2002 | Faries, Jr. et al. |
| 6,464,666 B1 | 10/2002 | Augustine |
| 6,467,953 B1 | 10/2002 | Faries, Jr. et al. |
| 6,524,239 B1 | 2/2003 | Reed et al. |
| 6,553,336 B1 | 4/2003 | Johnson et al. |
| 6,566,631 B2 | 5/2003 | Faries, Jr. et al. |
| 6,641,602 B2 | 11/2003 | Balding |
| 6,649,040 B1 | 11/2003 | Mirchi et al. |
| 6,660,974 B2 | 12/2003 | Faries, Jr. et al. |
| 6,722,782 B2 | 4/2004 | Faries, Jr. et al. |
| 6,736,788 B1 | 5/2004 | Mongomery et al. |
| 6,740,059 B2 | 5/2004 | Flaherty |
| 6,748,164 B1 | 6/2004 | Kuzyk |
| 6,768,085 B2 | 7/2004 | Faries, Jr. et al. |
| 6,788,885 B2 | 9/2004 | Mitsunaga |
| 6,788,997 B1 * | 9/2004 | Frederick ................... 700/236 |
| 6,824,528 B1 | 11/2004 | Faries, Jr. et al. |
| 6,850,252 B1 | 2/2005 | Hoffberg |
| 6,860,271 B2 | 3/2005 | Faries, Jr. et al. |
| 6,869,538 B2 | 3/2005 | Yu et al. |
| 6,967,575 B1 * | 11/2005 | Dohrmann et al. ........ 340/568.1 |
| 7,031,602 B2 | 4/2006 | Faries, Jr. et al. |
| 7,031,778 B2 | 4/2006 | Hsiung et al. |
| 7,041,941 B2 | 5/2006 | Faries, Jr. et al. |
| 7,090,658 B2 | 8/2006 | Faries, Jr. et al. |
| 7,176,030 B2 | 2/2007 | Faries, Jr. et al. |
| 7,238,171 B2 | 7/2007 | Faries, Jr. et al. |
| 7,262,698 B1 * | 8/2007 | Frederick et al. .......... 340/545.6 |
| 7,276,675 B2 | 10/2007 | Faries, Jr. et al. |
| 7,307,245 B2 | 12/2007 | Faries, Jr. et al. |
| 7,326,882 B2 | 2/2008 | Faries, Jr. et al. |
| 7,417,205 B2 | 8/2008 | Faries, Jr. et al. |
| 7,540,864 B2 | 6/2009 | Faries, Jr. et al. |
| 7,608,460 B2 | 10/2009 | Reed et al. |
| 7,611,504 B1 | 11/2009 | Faries, Jr. et al. |
| 7,726,876 B2 | 6/2010 | Laverdiere et al. |
| 7,740,611 B2 | 6/2010 | Faries, Jr. et al. |
| 7,942,851 B2 | 5/2011 | Faries, Jr. et al. |
| 8,226,293 B2 | 7/2012 | Faries, Jr. et al. |
| 8,226,605 B2 | 7/2012 | Faries, Jr. et al. |
| 8,313,462 B2 | 11/2012 | Faries, Jr. et al. |
| 2001/0009610 A1 | 7/2001 | Augustine |
| 2002/0081109 A1 | 6/2002 | Mitsunaga et al. |
| 2002/0156451 A1 | 10/2002 | Lenker |
| 2003/0000939 A1 * | 1/2003 | Faries et al. ................... 219/497 |
| 2003/0004470 A1 | 1/2003 | Hickerson et al. |
| 2003/0075183 A1 | 4/2003 | Faries, Jr. et al. |
| 2003/0135388 A1 | 7/2003 | Martucci et al. |
| 2003/0172937 A1 | 9/2003 | Faries, Jr. et al. |
| 2003/0216831 A1 | 11/2003 | Hart et al. |
| 2003/0222933 A1 | 12/2003 | Choi |
| 2004/0170409 A1 | 9/2004 | Faries, Jr. et al. |
| 2004/0189258 A1 | 9/2004 | Lehmann et al. |
| 2005/0059952 A1 | 3/2005 | Giuliano et al. |
| 2005/0070845 A1 | 3/2005 | Faries, Jr. et al. |
| 2005/0142013 A1 | 6/2005 | Faries, Jr. et al. |
| 2005/0222933 A1 | 10/2005 | Wesby |
| 2005/0242930 A1 * | 11/2005 | Nicolson et al. ......... 340/426.36 |
| 2006/0020255 A1 | 1/2006 | Cassidy et al. |
| 2006/0253075 A1 | 11/2006 | Faries, Jr. et al. |
| 2007/0000910 A1 | 1/2007 | Faries, Jr. et al. |
| 2007/0106243 A1 | 5/2007 | Faries, Jr. et al. |
| 2007/0142773 A1 | 6/2007 | Rosiello et al. |
| 2007/0161952 A1 | 7/2007 | Faries, Jr. et al. |
| 2007/0215018 A1 | 9/2007 | Faries, Jr. et al. |
| 2008/0021392 A1 | 1/2008 | Lurvey et al. |
| 2008/0147016 A1 | 6/2008 | Faries et al. |
| 2008/0205481 A1 | 8/2008 | Faries et al. |
| 2010/0111135 A1 | 5/2010 | Faries, Jr. et al. |
| 2010/0168671 A1 | 7/2010 | Faries, Jr. et al. |
| 2010/0222762 A1 | 9/2010 | Faries, Jr. et al. |
| 2010/0222763 A1 | 9/2010 | Faries, Jr. et al. |
| 2012/0053518 A1 | 3/2012 | Faries, Jr. et al. |
| 2012/0190105 A1 | 7/2012 | Faries, Jr. et al. |

FOREIGN PATENT DOCUMENTS

| | | |
|---|---|---|
| DE | 197 52 578 A1 | 6/1999 |
| GB | 2274514 A | 7/1994 |
| WO | 9221272 | 12/1992 |
| WO | 9845658 | 10/1998 |

OTHER PUBLICATIONS

CBi Healthcare Systems, Inc., *Controlled Temperature Cabinet System*, JEMS, Mar. 1997.

Koolatron, *P-34 PC-3 Precision Control Thermoelectric Cooler/Warmer*, Jan. 1998.

Koolatron, *Canadian company announces the release of a precision control unit*, Aug. 1997.

Anton, *500 miles from nowhere, it'll give you a cold drink or a warm burger...*, Technology Update, 1993.

Koolatron, *1997 U.S. $ Price List*, 1997.

Kellow et al, *Drug Adulteration in Prehospital Emergency Medical Services*, Oct. 1994.

CBi Medical, Inc., *IV Fluid Warmer Model 8362*, 1992.

\* cited by examiner

METHOD AND APPARATUS FOR SECURELY STORING MEDICAL ITEMS WITHIN A THERMAL TREATMENT SYSTEM

CROSS-REFERENCE TO RELATED APPLICATIONS

This application claims priority from U.S. Provisional Patent Application Ser. No. 60/783,389, entitled "Method and Apparatus for Securely Storing Medical Items Within a Thermal Treatment System" and filed Mar. 20, 2006, the disclosure of which is incorporated herein by reference in its entirety.

BACKGROUND OF THE INVENTION

1. Technical Field

The present invention embodiments pertain to systems for thermally treating medical items, such as the types of systems disclosed in U.S. Pat. No. 5,408,576 (Bishop), U.S. Pat. No. 6,259,067 (Faries, Jr. et al.), U.S. Pat. No. 6,294,762 (Faries, Jr. et al.), U.S. Pat. No. 6,376,805 (Faries, Jr. et al.), U.S. Pat. No. 6,384,380 (Faries, Jr. et al.), U.S. Pat. No. 6,467,953 (Faries, Jr. et al.), U.S. Pat. No. 6,566,631 (Faries, Jr. et al.), U.S. Pat. No. 6,640,974 (Faries, Jr. et al.), U.S. Pat. No. 6,722,782 (Faries, Jr. et al.), U.S. Pat. No. 6,768,805 (Faries, Jr. et al.) and U.S. Pat. No. 7,041,941 (Faries, Jr. et al.). The disclosures of the above-mentioned patents are incorporated herein by reference in their entireties. In particular, the present invention embodiments pertain to a locking mechanism for thermal treatment systems (e.g., systems heating and/or cooling solutions prior to the solutions being administered to the patient) or other medical equipment to secure medications being stored and/or thermally treated therein.

2. Discussion of Related Art

Various types of medical items require heating and/or cooling to a selected temperature prior to utilization in a medical procedure. Generally, the medical items may be heated and/or cooled for limited time intervals to preserve their effectiveness. These items typically include intravenous solutions, irrigation fluids, surgical instruments, bottles and blankets. Intravenous (IV) fluids, for example, are typically stored in a cool environment and, consequently, require heating to precise temperatures to prevent thermal shock and injury from occurring during infusion of the fluid into a patient. Similarly, irrigation fluids can be warmed or cooled to various temperatures depending upon their intended use. These types of fluids are typically provided to a patient utilizing a flexible bag or container filled with the fluid and delivered via a fluid line that conveys the fluid from the bag to the patient.

Some medical items can only be heated for a limited period of time, or in accordance with controlled warming cycles, in order to avoid adversely affecting their effectiveness. For example, some fluids, such as whole blood or fluids containing medication, should be warmed evenly to a specific temperature and can be rendered unusable or unsafe if all or a portion of the fluid is overheated. Various systems may be utilized to thermally treat these items, such as the systems disclosed in the aforementioned patents.

However, hospitals are currently required to secure medications during storage due to increased regulations. These regulations consider various solutions (e.g., including IV bags, irrigation bags, bottles, etc.) to be medications, thereby requiring these solutions to be similarly secured. The regulations cover the time period when the medications (e.g., IV bags, etc.) are being heated prior to use in a medical procedure and further mandate that medications be stored securely while being heated.

SUMMARY OF THE INVENTION

Accordingly, the present invention embodiments employ a locking mechanism for thermal treatment systems (e.g., systems heating and/or cooling solutions prior to the solutions being administered to the patient) or other medical equipment to secure medications being stored and/or thermally treated therein. The locking mechanism includes an integrated monitoring and display system to determine and indicate compliance with the regulations. The present invention embodiments control the distribution of medication and prevent unauthorized use that may lead to serious injury for a patient and/or an unauthorized recipient.

The above and still further features and advantages of the present invention will become apparent upon consideration of the following detailed description of specific embodiments thereof, particularly when taken in conjunction with the accompanying drawings, wherein like reference numerals in the various figures are utilized to designate like components.

DETAILED DESCRIPTION OF THE PREFERRED EMBODIMENTS

Figure 1:
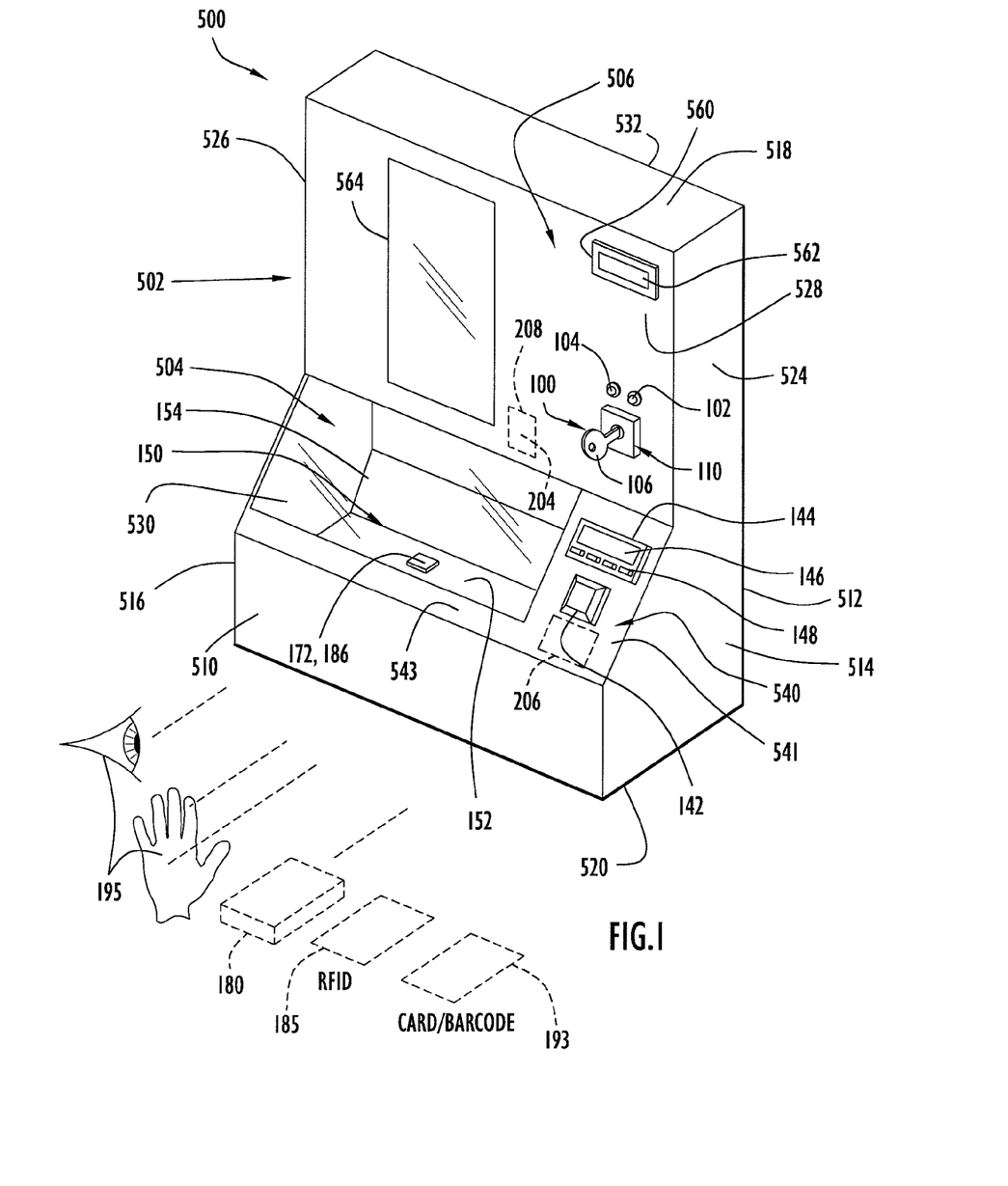
FIG. 1 is a view in perspective of an exemplary thermal treatment system including a locking mechanism according to an embodiment of the present invention.
Figure 2:
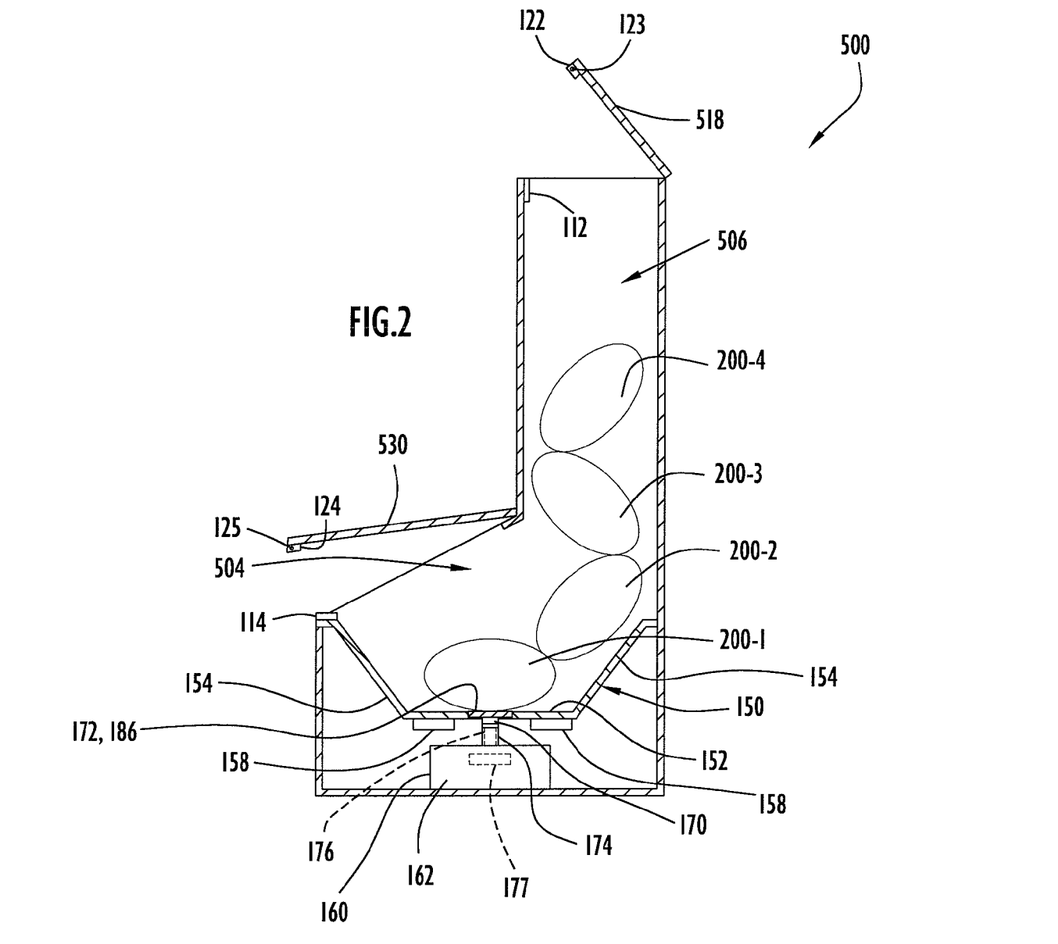
FIG. 2 is a side view in partial section of the thermal treatment system of FIG. 1.

An exemplary thermal treatment system employing the locking mechanism of a present invention embodiment is illustrated in FIGS. 1-2. Initially, the system is of the types disclosed in aforementioned U.S. Pat. No. 6,768,085 (Faries, Jr. et al.) and U.S. Pat. No. 7,041,941 (Faries, Jr. et al.). Specifically, system 500 includes a housing 502 including a heating compartment 504 and a storage compartment 506 disposed above the heating compartment. The heating compartment includes a front wall 510, a rear wall 512, side walls 514, 516, a bottom wall 520 and a front panel 540 that collectively define the heating compartment interior. A door 530 is disposed on the housing to cover a heating compartment open portion that facilitates placement and removal of items within the heating compartment as described below. Front and rear walls 510, 512 are substantially rectangular and are attached to and extend between side walls 514, 516. Front wall 510 has a height substantially less than that of rear wall 512. Bottom wall 520 is substantially rectangular and is attached to the bottom edges of the heating compartment front, rear and side walls. Side walls 514, 516 are generally rectangular with respective truncated upper front corner sections. The truncated section of side wall 514 includes an angled edge that extends from front wall 510 toward the storage compartment. The truncated section of side wall 516 includes a similarly angled edge.

Front panel 540 includes a control panel 541 and a projection 543. The control panel is substantially rectangular and is attached to front wall 510 and the angled edge of side wall 514. The control panel has a transverse dimension substantially less than the distance between side walls 514, 516 and is oriented at an angle toward rear wall 512 similar to that of the angled edge of side wall 514. Projection 543 is substantially rectangular and is attached to front wall 510, a control panel lower section and side wall 516. The projection extends from the front wall toward the storage compartment for a slight distance and is oriented at an angle similar to that of control panel 541. The open area between control panel 541, side wall 516 and projection 543 defines the heating compartment open portion.

Storage compartment 506 is disposed above heating compartment 504 and includes a top wall 518, side walls 524, 526 and front and rear walls 528, 532 that collectively define the storage compartment interior. Front and rear walls 528, 532 are substantially rectangular and are attached to and extend between side walls 524, 526. Front wall 528 extends from the upper edges of door 530 and control panel 541, while rear wall 532 extends from and is integral with heating compartment rear wall 512. Side walls 524, 526 are substantially rectangular and are attached to and extend between respective side edges of front and rear walls 528, 532. The side walls respectively extend from and are integral with respective heating compartment side walls 514, 516.

Top wall 518 is substantially rectangular and is attached to the upper edges of the storage compartment front, rear and side walls. Top wall 518 further provides access to the storage compartment and is typically pivotally connected to rear wall 532. The top wall opens upward from the storage compartment to enable placement and removal of medical solution containers within the system. Door 530 is typically pivotally connected to the lower portion of front wall 528 and opens upward from the heating compartment in order to provide access to the heating compartment for placement and removal of medical solution containers within that compartment. Top wall 518 and door 530 may both be partially or completely transparent to allow viewing of the storage and heating compartment interiors, respectively. Further, top wall 518 and/or door 530 may include any type of handle or latching mechanism to facilitate access to the system interior. The storage compartment basically houses medical solution containers 200-2 to 200-4 in addition to medical item 200-1 being thermally treated to enable the system to accommodate and heat plural containers as described below. In addition, the locking mechanism of a present invention embodiment locks top wall 518 and door 530 in closed states to secure medications (e.g., IV solution containers, etc.) within the system in accordance with regulations as described below.

Control panel 541 includes a power switch 142 and a controller 144 to indicate solution temperature and control operation of the system as described below. Controller 144 includes a display 146 (e.g., LED or LCD) and a plurality of input devices or buttons 148. The input devices are manipulable by a user to enable entry of a desired or set point temperature for a medical solution container placed within the housing compartment. Display 146 typically displays the measured temperature of the solution and may further be directed, via input devices 148, to display the desired or set point temperature. The controller receives a desired temperature from a user and controls heating of a medical solution to attain that temperature. The heating compartment houses a heating assembly to uniformly apply heat to a medical solution. The heating assembly includes a heating plate 150, a heater 158, a temperature sensor 172 and a limit switch 160. The heating plate includes a bottom wall 152 and side walls 154 extending at an angle from the bottom wall longer dimensioned side edges toward the interior surfaces of the heating compartment front and rear walls to form a generally 'U'-shaped heating plate configuration. Heater 158 is disposed on the bottom surface of the heating plate bottom wall. This arrangement facilitates rapid heating of a medical item which is especially advantageous during employment of the system in time critical situations, such as in an operating room. For example, the system may heat items to a desired temperature in the approximate range of 80° F. to 150° F. within a short time interval, generally within one hour (e.g., the particular time interval depends on various factors, such as initial item temperature, room temperature, selected desired temperature, etc.).

Limit switch 160 controls heater 158 in response to placement and removal of medical solution containers on the heating plate. Specifically, the limit switch is typically implemented in the form of a pressure type switch that enables or disables the heater in response to detection of pressure (e.g., the weight of a container) applied to a portion of the heating plate. However, the limit switch may alternatively be configured in any manner suitable for operation of the system. The limit switch includes a housing 162 and an arm 170. The limit switch housing is disposed beneath the heating plate bottom wall and includes a post or support member 174 extending from the housing top surface toward the heating plate. Arm 170 is attached in a cantilevered manner to the support member. Temperature sensors 172, 186 are mounted on arm 170 toward the arm distal end with wiring extending from the respective sensors to controller 144. Temperature sensor 186 basically measures excessive temperatures and serves as a cut-off switch. The arm extends from the support member along the underside of the heating plate bottom wall to align sensor 172 with an opening (not shown) defined in the heating plate bottom wall. The bottom wall opening provides temperature sensor 172 with access to a medical solution container placed on the heating plate. The limit switch arm is constructed of a resilient material that biases the arm toward the heating plate and enables the arm to move between that plate and the limit switch housing. The arm bias further forces the temperature sensor against a medical solution container placed on the heating plate, thereby facilitating an accurate temperature measurement. A contact member 176 is disposed on the limit switch housing coincident a distal portion of the limit switch arm and extends into the limit switch housing via an opening (not shown) defined in that housing. The contact member is typically directly attached to or resiliently biased toward the limit switch arm to enable movement of the contact member into or out of the limit switch housing in response to flexing of the limit switch arm.

The contact member is configured to actuate switch circuitry 177 disposed within the limit switch housing. In particular, the limit switch arm flexes toward the limit switch housing in response to pressure applied to the arm from a medical solution container placed on the heating plate. The contact member is subsequently urged into the housing and interfaces the switch circuitry. This motion results in actuation of the switch circuitry and effectively closes switch 160, thereby enabling heater 158. When a container is removed from the heating plate, arm 170 is biased toward the heating plate bottom wall with the contact member being withdrawn from the switch circuitry. This motion effectively results in disablement of the switch circuitry and effectively opens switch 160, thereby disabling the heater. The limit switch arm may further include a cut-out switch and/or additional temperature sensor 186 to facilitate disablement of the heater in response to excessive temperatures.

In addition, system 500 may further include a timer 560 to measure and display residence time of a medical item on heating plate 150 similar to the manner described in U.S. Pat. No. 7,041,941 (Faries, Jr. et al.). Specifically, timer 560 may be disposed on front wall 528 toward an upper front wall corner adjacent side wall 524. Timer 560 includes a display 562 to indicate the amount of time a medical item has resided on the heating plate. In other words, the timer measures and indicates the amount of time a medical item has been warmed by the system. The timer may be implemented by any conventional or other timing or time measuring devices and may include any conventional or other type of display (e.g., LED, LCD, etc.). Moreover, front wall 528 may further include a substantially rectangular window 564 disposed adjacent timer 560 to enable medical personnel to view and ascertain the quantity of medical items within storage compartment 506. The window may be of any shape or size, may be disposed at any suitable locations and may be constructed of any suitably transparent materials (e.g., glass, plastics, etc.).

Timer 560 is controlled by limit switch 160 to measure and indicate residence time in accordance with placement of a medical item on heating plate 150. Basically, when a medical item is urged by gravitational forces or manually manipulated onto the heating plate and limit switch, the limit switch enters a closed state and enables timer 560 to begin measuring elapsed time. The elapsed time is displayed on timer display 562, preferably in the format of hours, minutes and seconds. However, the elapsed time may be measured and/or displayed in any desired format or fashion (e.g., days, hours, minutes, seconds, etc.). The limit switch further actuates a time delay relay that delays operation of the heater for a predetermined time interval. This delay enables the temperature of temperature sensor 172 to approach the medical item temperature to provide enhanced temperature measurements. When the medical item is removed from the heating plate, the limit switch enters an open state, thereby causing the timer to reset via a reset relay as described below. The timer display notifies medical personnel of the residence time of a medical item on the heating plate. In other words, the timer informs medical personnel of the amount of time a medical item has been warmed. Since medical items typically have limits with respect to warming time, medical personnel may remove the warmed medical item prior to excessive heating of the medical item and reduction in effectiveness. Upon removal of a medical item from the heating plate, the next medical item within the storage compartment is gravitationally urged or manually manipulated onto the heating plate and the limit switch enters a closed state to start the timer and time delay as described above.

Figure 4:
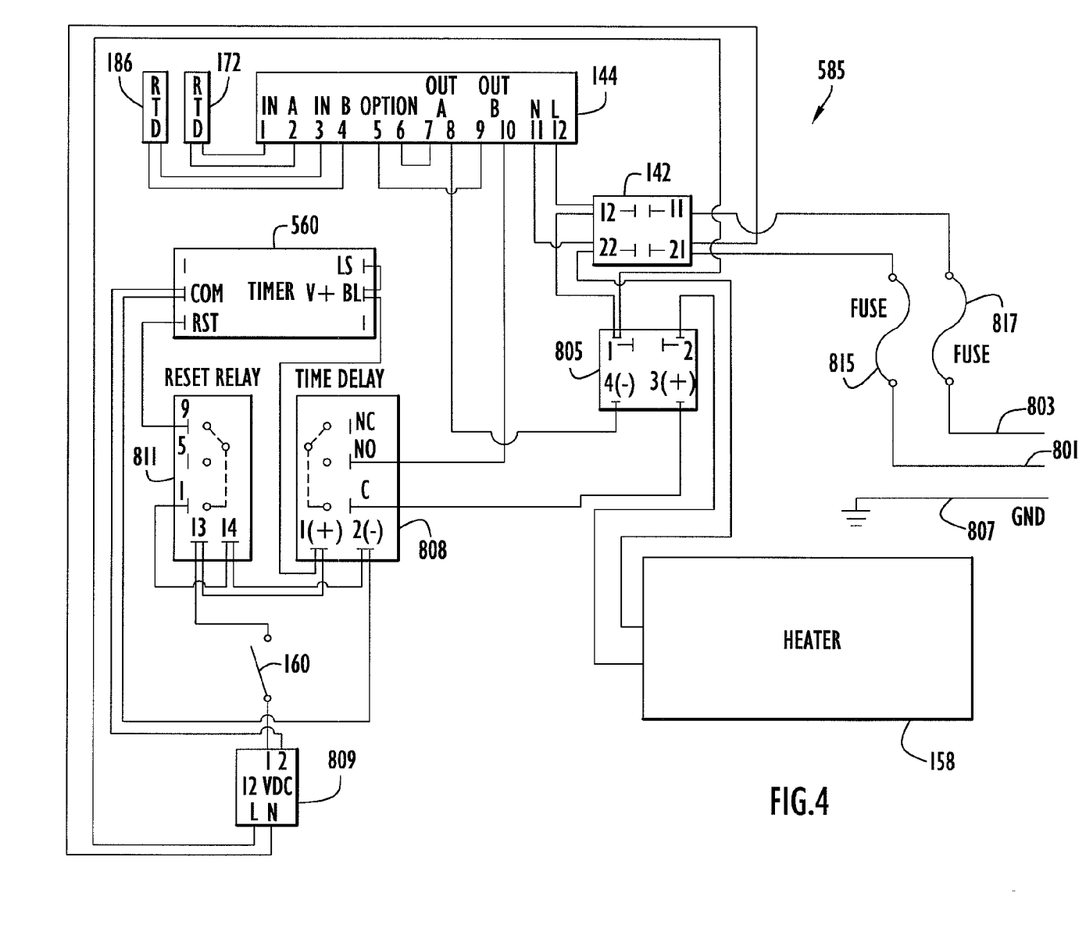
FIG. 4 is a schematic block diagram of an exemplary control circuit for the thermal treatment system of FIG. 1.

System 500 may employ control circuitry substantially similar to the control circuitry disclosed in U.S. Pat. No. 6,768,085 (Faries, Jr. et al.) and/or U.S. Pat. No. 7,041,941 (Faries, Jr. et al.). By way of example, an exemplary control circuit for system 500 is illustrated in FIG. 4. Specifically, control circuit 585 includes power switch 142, controller 144, limit switch 160, heater 158, temperature sensors 172, 186 and timer 560, each as described above. The circuitry further includes power conductors 801, 803, a solid state relay 805, a ground 807, a time delay relay 808, a reset relay 811 and a power source 809. Power conductors 801, 803 each include a respective fuse 815, 817 (e.g., a conventional 2 amp fuse) that is arranged in series with power switch 142 to prevent power surges from damaging the switch and circuitry. Power switch 142 controls power to the circuitry and is connected to the controller, solid state relay, power source and heater. The power switch may include a light to illuminate the switch. Controller 144 is further connected to solid state relay 805 and temperature sensors 172, 186. The controller controls power applied to the heater via relay 805 in accordance with a comparison of a temperature measured by temperature sensor 172 and a desired temperature entered into the controller by a user. In particular, controller 144 receives temperature signals from temperature sensor 172 indicating the temperature of a medical solution container in contact with the sensor (e.g., the container disposed on the heating plate surface). In response to the temperature measured by temperature sensor 172 being equal to or exceeding a desired temperature entered by a user, the controller disables power to the heater via solid state relay 805. Conversely, when the temperature measured by temperature sensor 172 is below the desired temperature, the controller enables power to the heater via the solid state relay.

Limit switch 160 is connected between power source 809 and reset relay 811 and facilitates control of the heater and timer in accordance with the presence of a medical solution container within the system. The power source is further connected to timer 560, while time delay relay 808 is connected to reset relay 811, controller 144 and solid state relay 805. The reset and time delay relays may be implemented by any conventional or other relay type devices. Basically, the limit switch enables the time delay and reset relays to control the timer and power to the heater. When a medical solution container is present on the heating plate, the limit switch is in a closed state as described above. Accordingly, the connection between the power source and reset relay is enabled. The reset relay controls the reset of timer 560. The timer basically resets when the reset line is low or grounded. Thus, when a medical item is removed from the heating plate and the limit switch enters an open state, the reset relay does not receive power from the power source and provides a low signal to the timer reset line, thereby facilitating a timer reset. When the limit switch enters a closed state due to the presence of a new medical solution container on the heating plate, the reset relay receives power signals from the power source, thereby providing a high signal to the timer reset line enabling the timer to operate. The reset relay further energizes the time delay relay which prevents solid state relay 805 from enabling the heater for a predetermined time interval. Preferably, the delay time interval is approximately 7.5 minutes, however, the time interval may be set to any desired interval. The time delay enables the temperature of temperature sensor 172 to approach the temperature of a new medical item received on the heating plate to enhance temperature measurement. Basically, the temperature of the temperature sensor is elevated due to contact with a warmed medical item. When the warmed medical item is removed from the system, the temperature sensor maintains the elevated temperature for a short interval. Thus, the temperature sensor in this state may provide elevated temperature readings relative to the actual temperature of a new unwarmed medical item placed on the heating plate. The time delay enables the temperature sensor to cool and provide accurate temperature measurements. Once the time delay interval has expired, time delay relay 808 enables the solid state relay to control the heater in accordance with control signals from the controller as described above.

When a medical solution container is removed or absent from the heating plate, the limit switch is in an open state and the connection between the reset relay and power source is disabled. The reset relay does not receive power and provides a low signal on the reset line of timer 560 to reset the timer.

Similarly, the time delay relay is without power and cannot energize solid state relay 805 to enable the heater. Thus, when the switch is in an open state indicating no medical item on the heating plate, the timer is reset and the heater is disabled.

Temperature sensor 186 is connected to the controller to facilitate disablement of the heater in response to detecting a temperature in excess of a predetermined threshold as described above. Basically, temperature sensor 186 provides a temperature indication of the solution container, heater and/or heating plate to controller 144. The controller disables power to the heater via relay 805 in response to the measured temperature exceeding a predetermined threshold as described above. Control circuit 585 may alternatively be implemented by any conventional circuitry components performing the above described functions, and may utilize a cut-off switch in place of temperature sensor 186 to disable the heater in response to excessive temperatures as described above.

As discussed above, medical regulations require hospitals to secure medications (e.g., including IV bags, irrigation bags, bottles, etc.) during storage. Accordingly, the present invention embodiments pertain to a locking mechanism to secure medications within thermal treatment systems. Initially, the locking mechanism may include a simple key lock to lock a corresponding system access door to a cabinet or compartment housing medical solution containers. However, in the event the system includes plural access doors as in the case of system 500, an electronic locking mechanism is preferably employed as described below. This enables one user mechanism to control plural access doors simultaneously and may be accomplished via an electronic key switch linked to electromagnetic solenoids. When the key is turned, the solenoids each retract a pin that is holding respective doors in a secure state as described below. The key switch may be configured to enable a reverse action of the key to lock the doors, and/or control the solenoids in response to a timer to hold the pin in place for enough time to allow the user to open the doors, add and or remove the necessary solution containers and close the doors before the solenoid pins are released.

Further, the locking mechanism of the present invention embodiments includes a monitoring and display system including indicator lights that allow for a visual representation indicating the locked or open states of the access doors and/or an audio system or alarm for alerting health care providers to the status of the locking mechanism. The indicator lights preferably include a green light to indicate an unlocked state and a red light to indicate a locked state. However, any suitable colors may be employed. The indicator lights may further flash. In addition, an audible alarm may be employed with the indicator lights to audibly indicate the status of the door locks.

Figure 5:
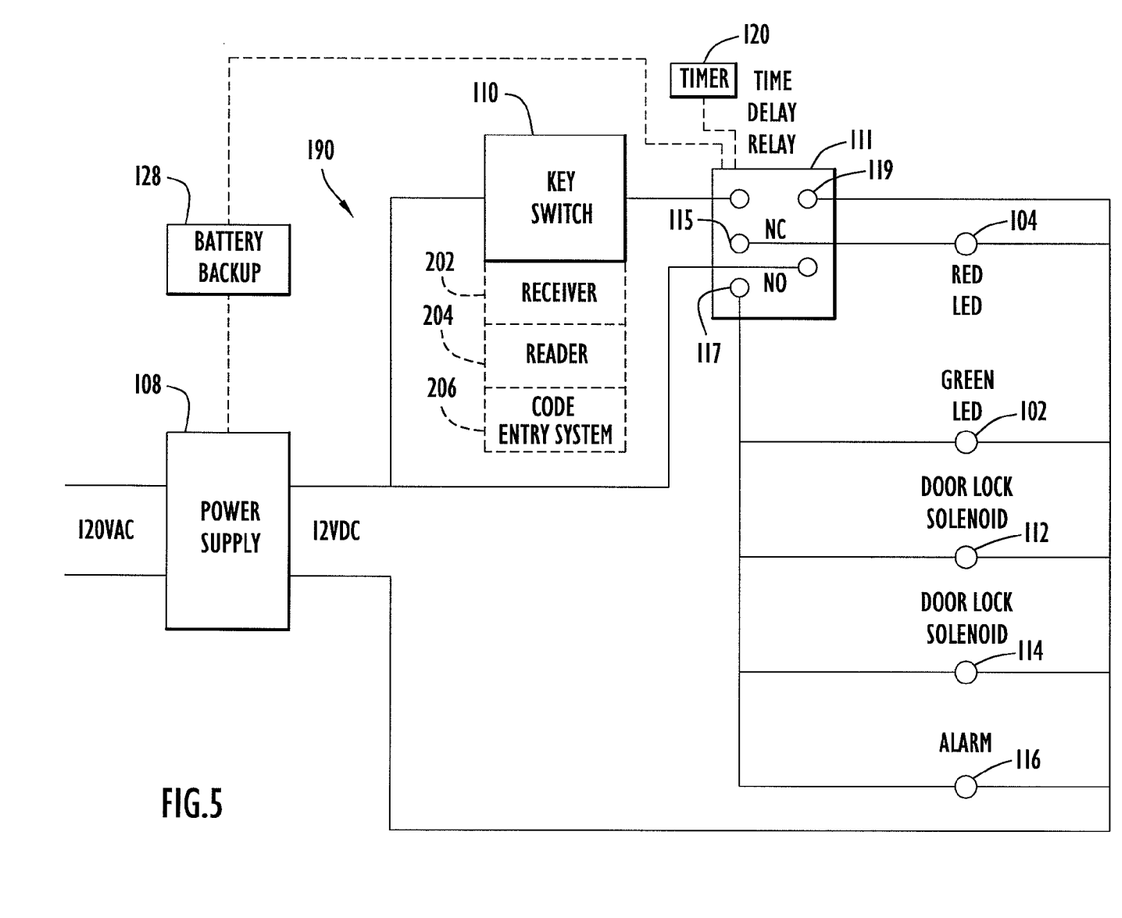
FIG. 5 is a schematic block diagram of an exemplary control circuit for the locking mechanism according to an embodiment of the present invention.

Referring back to FIGS. 1-3, system 500 includes a locking mechanism 100 according to a present invention embodiment to secure medications within the system and indicate a secure state of the system. The locking mechanism includes indicator lights 102, 104, a key 106, a key switch 110, solenoids 112, 114, and an alarm 116 (FIG. 5). Key switch 110 is disposed on front wall 528 of storage compartment 506 toward panel 541. The key switch may be implemented by any conventional or other switching device and includes a receptacle to receive corresponding key 106 therein. Rotation of the key enables key switch 110 to transition between states and control indicator lights 102, 104, solenoids 112, 114 and alarm 116 as described below. Indicator lights 102, 104 are disposed on front wall 528 above key switch 110. The indicator lights may be implemented by any conventional or other light emitting devices (e.g., LED, etc.). Indicator light 102 is preferably green to indicate an unlocked state of top wall 518 and door 530, while indicator light 104 is preferably red to indicate a locked state of the top wall and door.

Figure 3:
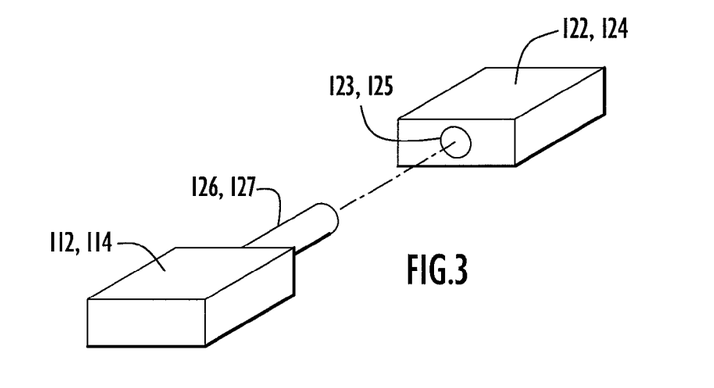
FIG. 3 is an exploded view in perspective of a solenoid of the locking mechanism of FIG. 1 selectively securing access to medical items within the thermal treatment system according to an embodiment of the present invention.

Solenoids 112, 114 are disposed within the system interior and are responsive to key switch 110 to lock and release top wall 518 and door 530, respectively. The solenoids may be implemented by any conventional or other electrical or electromagnetic devices. Solenoid 112 is disposed on the interior surface of an upper portion of front wall 528 proximate top wall 518. The solenoid controls projection and retraction of a pin 126 in accordance with the state of key switch 110. A projection 122 is attached to the interior surface of top wall 518 and includes an opening or aperture 123 defined therein. The dimensions of the aperture are sufficient to receive the solenoid pin therein. When the top wall is in a closed state, aperture 123 is disposed proximate solenoid 112, thereby enabling the solenoid to project the pin through the aperture to lock the top wall in response to manipulation of key 106 in a first direction. Solenoid 112 is typically biased in a state projecting the pin and retracts the pin in response to solenoid actuation. The key manipulation further illuminates red indicator light 104 to indicate a locked state. Conversely, retraction of the pin by solenoid 112 enables the top wall to enter an open state in response to manipulation of key 106 in a second or opposite direction. This key manipulation further illuminates green indicator light 102 and actuates alarm 116 (FIG. 5) to indicate an open state. Solenoid 112 and corresponding projection 122 are preferably disposed on the interior surfaces of the front wall and top wall toward a sidewall 524 or 526, but may be disposed at any suitable locations on the interior and/or exterior surfaces of the system to secure top wall 518.

Solenoid 114 is disposed on the interior surface of the lower portion of control panel 541 proximate front wall 510. The solenoid controls projection and retraction of a pin 127 in accordance with the state of key switch 110. A projection 124 is attached to the interior surface of door 530 and includes an opening or aperture 125 defined therein. The dimensions of the aperture are sufficient to receive the solenoid pin therein. When the door is in a closed state, aperture 125 is disposed proximate solenoid 114, thereby enabling the solenoid to project the pin through the aperture to lock the door in response to manipulation of key 106 in the first direction. Solenoid 114 is typically biased in a state projecting the pin and retracts the pin in response to solenoid actuation. The key manipulation further illuminates red indicator light 104 to indicate a locked state. Conversely, retraction of the pin by solenoid 114 enables the door to enter an open state in response to manipulation of key 106 in the second direction. This key manipulation further illuminates green indicator light 102 and actuates alarm 116 (FIG. 5) to indicate an open state. Solenoid 114 and corresponding projection 124 are preferably disposed on the interior surfaces of the control panel and door toward sidewall 516 or control panel 541, but may be disposed at any suitable locations on the interior and/or exterior surfaces of the system to secure door 530.

Alternatively, the locking mechanism may employ various manners to control locking and releasing of top wall 518 and door 530. For example, a wireless remote key system may be employed, where alarm 116 may audibly indicate the locked status of the top wall and door. In particular, locking mechanism 100 may include a remote control unit 180 and a receiver 202 (FIG. 5) disposed within system 500. Remote control unit 180 may be implemented by any conventional or other remote control units, such as those commonly utilized for automobile locks. Remote control unit 180, by way of example, may include buttons and an optional display. The remote control unit emits encoded command signals for processing by receiver 202 as described below. The remote control unit may include any conventional or other transmitter, and may transmit any type of energy (e.g., infrared, RF, ultrasonic, light, etc.). The receiver is preferably implemented by a conventional receiver compatible with the transmitter of the remote control unit.

Remote control unit 180 emits command signals to system 500, while receiver 202 embedded within the system receives the signals and controls indicator lights 102, 104, solenoids 112, 114 and alarm 116. Basically, solenoids 112, 114 project respective pins through apertures 123, 125 to lock the top wall and door in response to the receiver receiving a first command signal from remote control unit 180. This command signal further enables illumination of red indicator light 104 to indicate a locked state. Conversely, retraction of the respective pins by solenoids 112, 114 enables the top wall and door to enter an open state in response to receiver 202 receiving a second command signal from remote control unit 180. The second command signal further enables illumination of green indicator light 102 and actuation of alarm 116 (FIG. 5) to indicate an open state. The command signals may differ in any suitable characteristics (e.g., frequency, etc.) to indicate a desired operation.

Further, the locking mechanism of the present invention embodiments may alternatively employ an RFID key fob or badge 185 to lock and release the top wall and door. These may be implemented by any conventional or other devices. Receiver 202 may be configured to receive and process signals from badge 185 to control indicator lights 102, 104, solenoids 112, 114 and alarm 116 as described above (e.g., alternately transition the system between open and locked states) in response to signals from badge 185 indicating an authorized user (e.g., and ignoring signals from an unauthorized user).

In addition, the locking mechanism may employ a Smart Card, a magnetic swipe card or a bar coded item 193, or a biometric scan 195 (e.g., hand/finger print, retina, etc.) in combination with corresponding readers 204 (FIG. 5). The readers may be implemented by any conventional or other devices performing the desired scanning. Readers 204 are preferably located proximate a window 208 disposed on front wall 528 adjacent door 530. The readers may control indicator lights 102, 104, solenoids 112, 114 and alarm 116 in the manner described above in response to appropriate results indicating an authorized user from reading or scanning the items or user physical characteristics placed proximate window 208 (e.g., the locking mechanism basically ignores an unauthorized user). For example, the system may switch between open and locked states based on the appropriate authorized items or physical characteristics of authorized users being scanned.

Further, a code entry system 206 (FIG. 5) may be employed by the locking mechanism. The code entry system is preferably in the form of a keypad, cipher lock or voice/speech system. The keypad may be implemented by a conventional alphanumeric keypad with individual keys or a touch screen type display (with corresponding processor) providing areas representing alphanumeric or other characters for entering the code, while the cipher lock and voice systems may be implemented by any conventional or other code entry type systems. The code entry system is preferably disposed on control panel 541 adjacent power switch 142, but may disposed at any suitable locations. The code entry system may control indicator lights 102, 104, solenoids 112, 114 and alarm 116 in the manner described above in response to appropriate codes (e.g., personal identification number (PIN), password or pass code, etc.) entered by a user for locking and/or unlocking the system (e.g., the locking mechanism basically ignores unrecognized codes).

An exemplary control circuit for the locking mechanism according to a present invention embodiment is illustrated in FIG. 5. Initially, control circuit 190 may be independent of, coupled to or integrated with control circuitry 585 of system 500. Specifically, control circuit 190 includes indicator lights 102, 104, a power supply 108, key switch 110, a time delay relay 111, solenoids 112, 114 and alarm 116. The control circuit may alternatively include receiver 202, readers 204 and code entry system 206 depending upon the particular implementation of the locking mechanism. Power supply 108 may be implemented by any conventional or other power supply, and preferably receives power from a common wall outlet jack (e.g., 120V AC) to provide appropriate power signals (e.g., 12V DC) to circuit components. The power supply is preferably the same power supply utilized in control circuitry 585 of system 500.

Key switch 110 is coupled to the power supply and to time delay relay 111. The time delay relay is coupled to power supply 108 and to indicator lights 102, 104, solenoids 112, 114 and alarm 116. The time delay relay may be implemented by any conventional or other relay type components (e.g., electrical, mechanical, etc.), and includes output terminals 115, 117 and a reference terminal 119. The output terminals provide power to enable circuit components as described below. The reference terminal is coupled to the reference potential of the power supply and provides a reference potential or ground for each of the components coupled to terminals 115, 117. In particular, red indicator light 104 is disposed between output terminal 115 and reference terminal 119, while green indicator light 102, solenoids 112, 114 and alarm 116 are each disposed in parallel between output terminal 117 and reference terminal 119.

Key switch 110 is coupled between the positive terminal of power supply 108 and the time delay relay, and controls the time delay relay to actuate appropriate components in response to manipulation of key 106. In particular, manipulation of key 106 to lock top wall 518 and door 530 places key switch 110 in a first state. The key switch state controls the time delay relay to provide a positive potential on terminal 115 (e.g., and no potential on terminal 117). This produces a sufficient potential difference across red indicator light 104 (e.g., between output terminal 115 and reference terminal 119) to illuminate the red indicator light. In this case, since no sufficient potential difference exists between output terminal 117 and reference terminal 119, the solenoids and green indicator light are not actuated, where the solenoids remain or return to their biased state to project the pins and lock top wall 518 and door 530 as described above.

Manipulation of key 106 to open top wall 518 and door 530 places key switch 110 in a second state. The key switch state controls the time delay relay to provide a positive potential on terminal 117 (e.g., and no potential on terminal 115). This produces a sufficient potential difference across green indicator light 102, solenoids 112, 114 and alarm 116 (e.g., between output terminal 117 and reference terminal 119) to illuminate the green indicator light and actuate the solenoids and alarm. In this case, no sufficient potential difference exists between output terminal 115 and reference terminal 119 and the red indicator light is disabled. Since the solenoids are actuated, the pins are retracted and top wall 518 and door 530 may be opened as described above.

In addition, the key switch may be configured to control the solenoids in response to a timer 120 in order to actuate the solenoids to retract the pin for a predetermined time interval.

The time interval is sufficient to enable the user to open the top wall and/or door, add and/or remove the necessary solution containers and close the top wall and/or door before the solenoids return to their biased state to lock the top wall and door. In particular, key switch 110 is coupled to timer 120 and initiates the timer in response to conditions enabling actuation of solenoids 112, 114 to open the top wall and door. Key switch 110 actuates green light indicator 102, solenoids 112, 114 and alarm 116 in response to those conditions as described above. When timer 120 indicates expiration of the predetermined time interval, key switch 110 enables red light indicator 104, and disables the green light indicator, solenoids and alarm, thereby enabling the solenoids to return to their biased state to project the pins and lock the top wall and door as described above. The key switch further resets timer 120 and awaits manipulation of key 106 to re-initiate opening of the top wall and door as described above. The timer may be implemented by any conventional or other timing or time measuring devices, while the predetermined time interval may be any suitable time period (e.g., minutes, seconds, etc.).

Further, a battery backup system 128 is preferably employed in the control circuit to enable actuation of the solenoids to unlock the system in the event of a power failure in the facility. In particular, battery backup system 128 is coupled to power supply 108 and time delay relay 111. In the event of a power failure, battery backup system 128 detects this condition via power supply 108 (e.g., lack of power from the power supply) and controls time delay relay 111 to actuate solenoids 112, 114 (e.g., and green indicator light 102 and alarm 116) to open the top wall and door in substantially the same manner described above. The battery backup system may be implemented by any conventional or other backup power device or system.

Receiver 202, readers 204 and code entry system 206 may be disposed in control circuit 190 in substantially the same manner as key switch 110 to control time delay relay 111 to provide appropriate power signals to the components (e.g., indicator lights, solenoids, alarm, etc.) in accordance with desired user actions as described above.

Locking mechanism 100 may alternatively employ various devices to place top wall 518 and door 530 in a locked state. For example, locking mechanism 100 may include a gear motor or a pneumatic and/or hydraulic piston to project and retract pins through apertures 123, 125 in the manner described above. Further, the locking mechanism may include a magnetic latching system to hold the top wall and door closed using magnetism or magnetic forces. These alternative devices may be responsive to key switch 110, receiver 202, readers 204 or code entry system 206, depending upon the particular implementation, to lock and release top wall 518 and door 530 in substantially the same manner described above.

Operation of the present invention embodiments is described with reference to FIGS. 1-5. Specifically, a user selects one or more medical solutions (e.g., bags or bottles containing saline or IV solutions, antibiotics or other drugs, blood, etc.) for heating by the system and determines the appropriate temperature for the solution. The user subsequently activates power switch 142 and manipulates key 106, if necessary, to unlock top wall 518 and door 530. Alternatively, the user may enter various codes, present cards or physical attributes to the system to unlock the top wall and door as described above. The unlocked state is indicated by green indicator light 102 and alarm 116. The user pivots top wall 518 to an open state. The selected solution containers are placed into the system in stacked relation with an initial container disposed on plate 150 as described above.

Top wall 518 is subsequently pivoted to a closed state and the user manipulates the key or performs other appropriate actions to lock top wall 518 and door 530 as described above. The locked state is indicated by red light indicator 104. A desired temperature for the selected solutions is entered into controller 144 via controller input devices or buttons 148. The medical solutions within the storage compartment may be viewed through front wall window 564 as described above. In response to placement of a container on the heating plate bottom wall, the container engages temperature sensor 172 and causes closure of limit switch 160. The switch closure controls power to heater 158. The switch closure may further initiate timer 560 to continuously display the elapsed time to medical personnel on timer display 562 as described above. The heater applies heat to the heating plate bottom wall, while heating plate side walls 154 conduct heat from bottom wall 152 to evenly distribute heat to the initial container. A cut-out switch and/or temperature sensor 186 may be employed to facilitate disablement of the heater in response to excessive heater, heating plate and/or solution temperatures as described above.

Controller 144 displays the temperature of the container as measured by temperature sensor 172, and may alternatively display the desired or set point temperature entered by the user. In response to attaining the desired temperature, the user performs appropriate actions to unlock top wall 518 and door 530 as described above to enable removal of the initial container from the heating plate via door 530. The limit switch subsequently enters an open state, thereby resetting the timer and display. The user relocks the top wall and door, while a successive container is urged by gravitational forces and/or manually manipulated into position on the heating plate bottom wall. The limit switch enters a closed state and initiates operation of the timer and time delay to repeat the process for this container. The above process may be repeated for subsequent containers stored in the system. Once the last container is removed, the limit switch disables the heater until another container is placed on the heating plate as described above.

It will be appreciated that the embodiments described above and illustrated in the drawings represent only a few of the many ways of implementing a method and apparatus for securely storing medical items within a thermal treatment system.

The locking mechanism of the present invention embodiments may be utilized with any quantity of any types of thermal treatment systems for heating/cooling any fluids or any other medical items (e.g., bags or containers, saline solutions, intravenous (IV) or irrigation solutions, instruments, blankets, antibiotics or other drugs, blood, lines, cassettes, etc.), such as the types disclosed in the aforementioned patents. The locking mechanism may further be utilized with any type of medical equipment storing medications, and with any types of access members (e.g., doors, walls, panels, etc.). The thermal treatment system may include any conventional or other heating and/or refrigeration units to thermally treat the medical items to any desired temperature. The thermal treatment system may be powered by any conventional or other power source (e.g., AC, DC, wall outlet jack, batteries, etc.).

The housing and housing components of the thermal treatment system (e.g., panels, walls, etc.) may be of any size, shape or configuration and may be constructed of any suitable materials. Any portion of the housing may be constructed of a transparent material. The heating and storage compartments may be of any quantity, shape or size and may hold any quantity of medical solution containers or other items (e.g., one or more containers or items). The top wall and door may be of any quantity, shape or size, may be constructed of any suitable materials, and may be connected to the housing at any suitable locations in any fashion to pivot in any desired direction and/or manner (e.g. hinged doors, sliding doors, removable panel doors, etc.). Further, the door and top wall may include a window of any size or shape, while the door, top wall and/or window may be constructed of any translucent, transparent or other materials. The door and top wall may include any quantity of any type of handle or latching mechanism disposed at any suitable locations. The housing may include any types of openings, mechanisms, devices, access members or other techniques to provide access to the housing interior.

The thermal treatment system may warm and/or cool any quantity of any type of medical solution container or other item to any desired temperature. The controller may be implemented by any conventional or other microprocessor or controller and may be disposed on or within the system at any suitable locations. The controller may control the heater to any desired temperature. The controller or system may include any quantity of any type of input device (e.g., keys, buttons, mouse, voice, touch screen, etc.) to facilitate entry of any desired temperatures or any other information. The controller may include or control any quantity of any type of display of any shape or size to convey any desired information. The display may be integral with or detached from the controller or system and may include an LED, LCD or monitor type display, indicator lights, or any other mechanism for indicating desired and/or measured temperature or any other information. Further, the display may include any type of buttons or data entry devices to program the controller in any manner. The controller may employ any conventional or other control algorithms (e.g., fuzzy logic, PID, etc.). The system may include any quantity of heating assemblies and any quantity of controllers to accommodate the heating assemblies, where each controller may accommodate one or more heating assemblies.

The heating plate may be of any quantity, shape, size or configuration to heat a medical solution or other item. The heating plate may include any quantity of conducting and/or non-conducting walls of any shape or size and may be constructed of any suitable materials. The heater may be implemented by any quantity of any conventional heater or other heating device (e.g., conduction, convection, microwave or other radiation, etc.). The heating plate may include any quantity of heaters of any shape or size arranged in any configuration (e.g., strips, annular, segments, etc.) and disposed at any suitable locations for applying heat. The heater may be attached to the heating plate via any conventional or other fastening technique (e.g., pressure sensitive or other adhesives, etc.). The system may alternatively include any quantity of heaters of any shape or size disposed at any suitable locations on the heating plate or within the systems.

The temperature sensors may be implemented by any quantity of any type of conventional or other temperature measuring device (e.g., RTD, infrared, etc.) and may be disposed at any suitable locations on the arm, heating plate or within the system. The cut-out switch may be implemented by any quantity of any type of conventional or other limiting device and may be utilized for any desired temperature or threshold. The cut-out switch may be utilized in combination with the additional temperature sensor to facilitate disablement of the heater in response to any desired temperature or temperature range. The cut-out switch and/or additional sensor may be disposed at any locations on the arm, heating plate or within the systems and may measure the temperature of any system objects (e.g., heating plate, medical item, heater, etc.). Alternatively, a single temperature sensor may be employed to facilitate control of the heater in response to measured medical item and excessive heater temperatures.

The limit switch may be implemented by any quantity of any type of pressure or other switch and/or switch/sensor combination for detecting the presence of a medical solution container or other item and actuating or disabling a circuit. The limit switch may include any types of mechanical, electrical and/or chemical switching mechanisms or any combinations thereof. The limit switch may be positioned at any location proximate the heating plate or within the system to detect the presence of a medical solution container or other item. The limit switch components (e.g., housing, arm, support member, contact member, etc.) may be of any shape or size and may be constructed of any suitable materials. The arm may support any quantity of any types of sensing devices. The switching circuitry may include any conventional or other circuitry or mechanical and/or electrical components that accommodate the contact member to establish or remove a circuit connection (e.g., open or close a circuit).

The control circuit of the thermal treatment system may be implemented by any quantity of any conventional or other electrical components arranged in any fashion and performing the functions described above. The circuit may be disposed at any location on or within the housing and may be arranged in any fashion. The power switch, controller, display, input devices and indicators may be disposed at any suitable locations on or within the housings. The fuses may be implemented by any conventional or other fuses or limiting devices configured for any desired current level.

The thermal treatment system may be used at any suitable locations (e.g., hospital or other medical facility, emergency medical or other vehicles, etc.) with any types of power sources (e.g., AC, DC, wall outlet jack, batteries, vehicle power system, etc.) to heat any quantity of any type of medical solution container or other item. The systems preferably heat items to desired temperatures within the approximate range of 80° F.-150° F., but may be utilized to heat the items to any desired temperatures or temperature ranges.

The storage compartment and door window may be of any shape or size and may be disposed at any suitable locations. The window may be constructed of any suitable materials (e.g., glass, plastic, etc.) and include any desired degree of transparency.

The timer of the thermal treatment system may be implemented by any conventional or other timing or timer devices (e.g., processors, hardware or other circuitry and/or software, etc.). The timer may be disposed at any suitable locations on or in proximity to the system. The timer may include any type of conventional or other display (e.g., LED, LCD, etc.) integral with or remote from the timer or system. The timer or controller may be initiated by the limit switch and/or manually by a user via control or input devices (e.g., keys, buttons, etc.) to initiate time measurement. The timer may increment or decrement time to measure elapsed time and may measure and/or display the time in any desired format or time units (e.g., hours, minutes, seconds, etc.). The system may further include visual and/or audio alarms to notify a user when a particular time interval expired, or disable heating upon expiration of that time interval. The system may include any quantity of timers or controllers to measure and/or display various time intervals (e.g., timer to measure residence time within the system or storage compartment, timer to measure residence time on heating plate, etc.).

The system control circuit relays (e.g., time delay, reset, etc.) may be implemented by any conventional or other relays or circuitry. The reset relay may provide any signal to the timer to facilitate a reset. The time delay relay or controller may be set to provide any desired time delay in any desired time units (e.g., minutes, seconds, etc.). The power sources may be implemented by any conventional or other power sources or circuitry and may provide any desired power signal (e.g., 12V DC, AC, voltage, current, etc.).

The thermal treatment system and/or the limit switch may be responsive to a particular weight of or pressure exerted by a medical item (e.g., to initiate heating, residence time measurements, etc.). For example, the limit switch may enter a closed state in response to a medical item having at least a desired weight or exerting at least a certain pressure against the switch. This enables the system to accommodate and discriminate between particular medical items (e.g., a system for heating three liter medical solution bags does not operate for one liter medical solution bags).

The locking mechanism may be disposed at any suitable locations on and/or within a system. The solenoids may be implemented by any quantity of any conventional or other electrical, mechanical or electromagnetic devices to secure doors in a closed state. The solenoids may be disposed at any suitable locations and engage any suitable members on the door, top wall and/or system to secure the doors. The projections may be of any shape or size, may be disposed at any suitable locations and may include any quantity of openings of any shape or size defined therein at any suitable locations.

The key switch may be implemented by any conventional or other switching device, and may be manipulated by any suitable object (e.g., key, card, etc.). The switch states may be associated in any fashion with any desired manipulation of the key (e.g., rotation in any direction, etc.). The key switch may be of any shape or size, and may be disposed at any suitable locations.

The indicator lights may be of any quantity, shape, size or color, and may be disposed at any suitable locations. The color of the light indicators may be associated with any desired states or conditions in any fashion. The light indicators may be implemented by any conventional or other light emitting devices, where one or more colors or light indicators may be associated with a state or condition. The light indicators may emit light in any fashion (e.g., pulsed or flashing, continuous, etc.). The alarm may be of any quantity, may be implemented by any conventional or other audio or sound emitting devices, and may be disposed at any suitable locations. The alarm may be actuated in response to any desired conditions (e.g., open, closed, etc.) and may emit sound in any fashion (e.g., pulsed or beeps, continuous, in combination with the light indicators, etc.). The locking mechanism may actuate the light indicators and alarm in any fashion with respect to each other (e.g., simultaneously, interleaving, individually, etc.).

The locking mechanism may employ any suitable techniques, either individually or in any combinations, to enable a user to lock or unlock the system (e.g., mechanical key or other lock, key switch, wireless remote, RFID key fob or badge, Smart Card (e.g., a card with any processing device or circuit), a magnetic swipe card, a biometric scan, a finger print, hand print and/or retina scan, a barcode scan, manual and/or verbal entry of a code, etc.). The various item manipulations or identifications within these techniques may be utilized in any fashion to lock and/or unlock the system (e.g., different manipulations of the key or different codes or physical characteristics may be associated with locking or unlocking of the system, successive identifications of an item or code may alternately transition the system between locked and unlocked states, etc.). The receivers, readers and code entry devices may be implemented by any quantity of any conventional or other components compatible with the mechanisms employed by a user to control the lock mechanism (e.g., finger, hand or other physical scanner, bar code reader, keypad, cipher lock, touch screen display, card reader, receiver, voice and/or speech recognition system (e.g., with audio receiving device and processor), etc.). These devices may be disposed at any suitable locations on or within the system to obtain the information from a user.

The remote control unit may be of any shape or size and may emit any desired energy signals (e.g., IR, etc.). The remote control unit may be implemented by any conventional or other remote control units (e.g., automobile remote control units, etc.). The window receiving articles to be scanned may be of any quantity, shape or size, may be constructed of any suitable materials of any desired degree of transparency and may be disposed at any suitable locations. The code entry system may be implemented by any suitable device or system enabling entry of a code (e.g., cipher lock, keypad, touch screen display, voice and/or speech recognition system (e.g., with a microphone or other audio receiving device), etc.). The code may be of any desired type or length and may include any quantity of words or alphanumeric or other characters (e.g., PIN, password or pass phrase, command, etc.) and may enable locking and/or unlocking. The code may entered in any desired fashion (e.g., verbally and/or manually, etc.) and may be pre-assigned and/or selected and/or modified by a user. The voice recognition/speech system may further identify an authorized user voice (e.g., with or without a pass code or password) prior to locking or unlocking the thermal treatment system.

The locking mechanism control circuit may include any quantity of any conventional or other components (e.g., power supply, relay, switch, indicators, alarm, solenoids, receivers, readers, keypads, cipher locks, code entry system, battery backup, timer, etc.) arranged in any fashion. The control circuit may be disposed at any suitable locations within the system. The control circuit may be an individual circuit, or be integrated or coupled with a system control circuit.

The time delay relay of the locking mechanism may be implemented by any conventional relay device, and may control the mechanism components (e.g., indicator lights, solenoids, alarm, etc.) in any fashion in response to the switch states, output from alternative devices (e.g., reader, receiver, keypad/cipher, code entry system, etc.) or any other conditions (e.g., power loss, expiration of a time interval, etc.). Any suitable potentials or voltages may be applied to the terminals (e.g., output terminals, reference terminal, etc.) to control the mechanism components.

The timer of the locking mechanism may be implemented by any conventional or other timing or timer devices (e.g., processors, hardware or other circuitry and/or software, etc.). The timer may increment or decrement time to measure elapsed time and may measure and/or display the time in any desired format or time units (e.g., hours, minutes, seconds, etc.). The locking mechanism may further include visual and/or audio alarms to notify a user when a particular time interval expired and the system becomes locked. The timer may receive any suitable signals for a reset or to initiate time measurement, and provide any suitable signals to indicate expiration of a time interval or an amount of elapsed time.

The battery backup system may be implemented by any conventional or other power system. The battery backup system may provide any suitable power signals and control any locking mechanism components in any fashion in response to a power interruption or failure (e.g., open the system, generate an alarm, etc.). The battery backup system may detect a power failure or interruption in any suitable manner (e.g., no or low power for a predetermined time interval, etc.).

The locking mechanism may control any quantity of access doors of a system individually (e.g., each access door may be in a different state), where each access door may provide access to the same or different compartments. Alternatively, the locking mechanism may control any quantity of access doors collectively, where each access door is in the same state (e.g., open or closed).

The locking mechanism may employ any suitable types of locks to lock access doors to a system. For example, simple mechanical locks may be employed for each access door or compartment. Alternatively, electrical locking mechanisms may be employed to control access doors. Further, the locking mechanism may employ any suitable devices to secure access doors in a locked state (e.g., electromagnetic devices, pneumatic and/or hydraulic mechanisms, magnetic mechanisms, etc.). Moreover, the locking mechanism may unlock system doors for any predetermined time interval (e.g., minutes, hours, etc.) to provide an interval to load and/or unload medical items from the system.

It is to be understood that the terms "top", "bottom", "front", "rear", "side", "height", "length", "width", "upper", "lower" and the like are used herein merely to describe points of reference and do not limit the present invention embodiments to any particular orientation or configuration.

The present invention embodiments are not limited to the applications or systems described above, but may be utilized with any medical or other items and any thermal treatment or other medical systems to secure items therein and indicate and display a secure status.

From the foregoing description, it will be appreciated that the invention makes available a novel method and apparatus for securely storing medical items within a thermal treatment system, wherein a locking mechanism for thermal treatment systems (e.g., systems heating and/or cooling solutions prior to the solutions being administered to the patient) or other medical equipment secures medications being stored and/or thermally treated therein.

Having described preferred embodiments of a new and improved method and apparatus for securely storing medical items within a thermal treatment system, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system for thermally treating and securely maintaining medical items comprising:
    a housing;
    a thermal treatment unit disposed within said housing and including a compartment to receive and thermally treat at least one medical item therein, wherein said housing includes a plurality of access members each enabling access from external of said housing to said compartment and said at least one medical item; and
    a common locking mechanism to selectively transition each of said access members of said housing between open and secured states in response to user manipulation of said locking mechanism and to indicate said state of each of said access members, wherein said locking mechanism includes:
        a plurality of lock units each associated with a corresponding access member of said housing to transition that access member between said open and secured states, wherein each lock unit includes a locking device attached to a housing interior surface proximate a corresponding access member to manipulate an engagement member and a projection attached to and extending from an interior surface of said corresponding access member with an aperture defined therein to receive said engagement member;
        a control unit to generate a signal common to each of said plurality of lock units that triggers transition of each of said plurality of access members of said housing to a common state in response to user manipulation of said locking mechanism, wherein said common state includes one of said open state and said secured state, and wherein said common signal includes a first signal to withdraw said engagement member from said aperture and transition each said lock unit to said open state in response to a first user manipulation of said locking mechanism and a second different signal to enable insertion of said engagement member within said aperture and transition each said lock unit to said secured state in response to a second user manipulation of said locking mechanism;
        an indicator to indicate said common state of each of said plurality of access members of said housing;
        a time delay relay to actuate said engagement members in accordance with a predetermined time delay; and
        a backup power system to detect a power failure and to control said time delay relay to actuate said engagement members to transition said access members from said secured state to said open state in response to said detection of said power failure.

2. The system of claim 1, wherein said locking mechanism includes a key switch and a corresponding key, and wherein said control unit generates said common signal in response to said key being received in said key switch and manipulated by a user to selectively transition said access members between said open and secured states.

3. The system of claim 1, wherein said locking mechanism includes a receiver to receive transmitted signals, and wherein said control unit generates said common signal to selectively transition said access members between said open and secured states in response to said receiver receiving control signals from a transmitting device.

4. The system of claim 3, wherein said transmitting device includes at least one of an RFID device and a remote control unit.

5. The system of claim 1, wherein said locking mechanism includes a reader unit to examine an item and said control unit generates said common signal to selectively transition said access members between said open and secured states in response to said reader unit identifying said item enabling said transition.

6. The system of claim 5, wherein said reader includes a bar code reader and said item includes a bar code enabling said transition.

7. The system of claim 5, wherein said reader includes a card reader and said item includes at least one of a card with a processing device and a magnetic card enabling said transition.

8. The system of claim 5, wherein said reader includes a scanner and said item includes a physical characteristic of an authorized user.

9. The system of claim 8, wherein said physical characteristic includes at least one of a fingerprint, handprint and a retina.

10. The system of claim 1, wherein said locking mechanism includes a code entry device to enable entry of a code by a user and said control unit generates said common signal to selectively transition said access members between said open and secured states in response to said code entry device receiving an appropriate code for said transition.

11. The system of claim 10, wherein said code entry device includes at least one of a keypad, a cipher lock system, a voice recognition system and a speech recognition system.

12. The system of claim 10, wherein said code entry device includes a touch screen display.

13. The system of claim 1, wherein each said locking device includes a solenoid and said engagement member includes a retractable pin to engage said projection of said corresponding access member and place that access member in said secured state.

14. The system of claim 1, wherein said locking mechanism transitions said access members to said open state from said secured state for a predetermined time interval and returns said access members to said secured state in response to expiration of said predetermined time interval.

15. The system of claim 1, wherein said at least one medical item includes a medical solution.

16. The system of claim 1, wherein said indicator includes at least one of a visual indicator and an audio device to indicate said common state of said access members.

17. The system of claim 16, wherein said visual indicator includes a plurality of light emitting devices each associated with a corresponding state of said access members.

18. A method for securely maintaining medical items within a thermal treatment system including a housing, a thermal treatment unit disposed within said housing and including a compartment to receive and thermally treat at least one medical item therein, wherein said housing includes a plurality of access members and each access member enables access from external of said housing to said compartment and said at least one medical item, the method comprising:
(a) selectively transitioning each of said access members of said thermal treatment system housing between open and secured states via a common locking mechanism in response to user manipulation of said locking mechanism, wherein said locking mechanism includes a plurality of lock units each associated with a corresponding access member of said housing to transition that access member between said open and secured states, wherein each lock unit includes a locking device attached to a housing interior surface proximate a corresponding access member to manipulate an engagement member and a projection attached to and extending from an interior surface of said corresponding access member with an aperture defined therein to receive said engagement member, and step (a) further includes:
(a.1) generating a signal common to each of said plurality of lock units that triggers transition of each of said plurality of access members of said housing to a common state in response to user manipulation of said locking mechanism, wherein said common state includes one of said open state and said secured state, wherein said common signal includes a first signal to withdraw said engagement member from said aperture and transition each said lock unit to said open state in response to a first user manipulation of said locking mechanism and a second different signal to enable insertion of said engagement member within said aperture and transition each said lock unit to said closed state in response to a second user manipulation of said locking mechanism, and wherein said engagement members are actuated in accordance with a predetermined time delay via a time delay relay;
(b) indicating said common state of each of said plurality of access members via an indicator; and
(c) detecting a power failure via a backup power system and controlling said time delay relay to actuate said engagement members to transition said access members from said secured state to said open state in response to said detection of said power failure.

19. The method of claim 18, wherein said locking mechanism includes a key switch and a corresponding key, and step (a.1) further includes:
(a.1.1) receiving said key within said key switch and generating said common signal to selectively transition said access members between said open and secured states in response to user manipulation of said key.

20. The method of claim 18, wherein said locking mechanism includes a receiver to receive transmitted signals, and step (a.1) further includes:
(a.1.1) generating said common signal to selectively transition said access members between said open and secured states in response to said receiver receiving control signals from a transmitting device.

21. The method of claim 20, wherein said transmitting device includes at least one of an RFID device and a remote control unit.

22. The method of claim 18, wherein said locking mechanism includes a reader unit to examine an item, and step (a.1) further includes:
(a.1.1) generating said common signal to selectively transition said access members between said open and secured states in response to said reader identifying said item enabling said transition.

23. The method of claim 22, wherein said reader includes a bar code reader, and step (a.1.1) further includes:
(a.1.1.1) generating said common signal to selectively transition said access members between said open and secured states in response to said bar code reader identifying a bar code enabling said transition.

24. The method of claim 22, wherein said reader includes a card reader, and step (a.1.1) further includes:
(a.1.1.1) generating said common signal to selectively transition said access members between said open and secured states in response to said card reader identifying at least one of a card with a processing device and a magnetic card enabling said transition.

25. The method of claim 22, wherein said reader includes a scanner, and step (a.1.1) further includes:
(a.1.1.1) generating said common signal to selectively transition said access members between said open and secured states in response to said scanner identifying a physical characteristic of an authorized user.

26. The method of claim 25, wherein said physical characteristic includes at least one of a fingerprint, handprint and a retina.

27. The method of claim 18, wherein said locking mechanism includes a code entry device to enable entry of a code by a user, and step (a.1) further includes:
(a.1.1) generating said common signal to selectively transition said access members between said open and secured states in response to said code entry system receiving an appropriate code for said transition.

28. The method of claim 27, wherein said code entry device includes at least one of a keypad, a cipher lock system, a voice recognition system and a speech recognition system.

29. The method of claim 27, wherein said code entry device includes a touch screen display.

30. The method of claim 18, wherein each said locking device includes a solenoid and said engagement member includes a retractable pin, and step (a.1) further includes:
- (a.1.1) engaging said projection of said corresponding access member with said pin to place that access member in said secured state.

31. The method of claim 18, wherein step (a.1) further includes:
- (a.1.1) transitioning said access members to said open state from said secured state for a predetermined time interval and returning said access members to said secured state in response to expiration of said predetermined time interval.

32. The method of claim 18, wherein said at least one medical item includes a medical solution.

33. The method of claim 18, wherein step (b) further includes:
- (b.1) indicating said common state of said access members via at least one of a visual indicator and an audio device.

34. The method of claim 33, wherein said visual indicator includes a plurality of light emitting devices each associated with a corresponding state of said access members.

\* \* \* \* \*